United States Patent [19]

Nordh

[11] 4,243,693
[45] Jan. 6, 1981

[54] METHOD AND COMPOSITION FOR THE PRESERVATION OF PLANTS

[76] Inventor: Sven B. L. Nordh, Månskensgatan 51, S-260 35 Ödåkra, Sweden

[21] Appl. No.: 43,630

[22] Filed: May 30, 1979

[51] Int. Cl.³ .................. A01G 5/06; A01N 1/00; A01N 3/00
[52] U.S. Cl. .................. 427/4; 47/DIG. 2; 47/58; 252/383; 428/22
[58] Field of Search .................. 427/4; 428/22; 8/3; 47/DIG. 2, 58; 252/383

[56] References Cited

U.S. PATENT DOCUMENTS

| | | | |
|---|---|---|---|
| 1,410,226 | 3/1922 | Segall | 8/3 |
| 1,484,656 | 2/1924 | Koropp et al. | 428/22 |
| 1,714,838 | 5/1929 | Anderson | 8/3 |
| 1,908,922 | 5/1933 | Ruzicka | 427/4 |
| 3,895,140 | 7/1975 | Sheldon et al. | 427/4 |

FOREIGN PATENT DOCUMENTS

| | | |
|---|---|---|
| 14825 of 1897 | United Kingdom | 427/4 |
| 12835 of 1901 | United Kingdom | 427/4 |

OTHER PUBLICATIONS

Expenment Station Record, vol. 18, No. 1, 1906, p. 44.
New York Times, Sun. May 17, 1959, Section 2, (Gardens), p. 24x.

*Primary Examiner*—Ronald H. Smith
*Assistant Examiner*—S. L. Childs
*Attorney, Agent, or Firm*—Irvin A. Lavine

[57] ABSTRACT

Living plants, in particular coniferous plants, with the exception of Picea, Abies, Tsuga, Larix, Taxus and Cedrus genuses, are preserved by having them suck up a preservative liquid which is based on glycerin and water in volume proportions of 18:82 to 35:65 and contains dyestuffs for replacing the color of the plant parts after preservation. The dyestuffs are to comprise, apart from a blue and possibly also a red dyestuff, tartrazine (C.I. 19140, E102) in a concentration of from 2–10 g/l of preservative liquid. The blue dyestuff comprises preferably patent blue V (C.I. 42051, E131) in a concentration of from 0.1 to 0.8 g/l and the red dyestuff most preferably of new coccine (C.I. 16255, E124) in a concentration of from 1 to 20 g/l. The relative concentrations between the different dyestuffs are adapted into conformity with the sought-for color of the preserved plant. The preservative liquid may advantageously also contain a water-soluble potassium salt, preferably potassium nitrate in a concentration of from 1 to 15 g/l. The preservation is effected at a temperature of from 15° to 33° C. in a current of air at a relative humidity of at most 60%, the preservative liquid preferably being a few degrees centigrade warmer than the current of air.

25 Claims, No Drawings

METHOD AND COMPOSITION FOR THE PRESERVATION OF PLANTS

The present invention relates to a method and a composition for the preservation of living plants, that is to say convert a living plant to the dead state without changing, to any appreciable extent, the natural appearance or character of the plant. The invention is particularly, but not exclusively, intended for coniferous plants with the exception of the Picea, Abies, Tsuga, Larix, Taxus and Cedrus genuses.

It is known from, for example, French Pat. Nos. 1,105,091 and 2,160,310, German Pat. No. 213,877, German Offenlegungsschrift No. 1,542,903 and the publication "Garden Flowers," Compton, J., Stockholm 1970, pp. 148 and 149, to use mixtures of glycerin and water for preserving plants, that is to say to arrest the dissolution of the plants cells (and thereby the plant) into other component parts after the death of the plant. Even though it has been possible to realize a certain preservation and retain a certain natural appearance in plants by means of these prior art processes, preservation has, nevertheless, been far too limited and restricted to warrant the introduction of industrial manufacture. Moreover, in most cases the natural resilience and flexibility of the plants has been partly lost. In the prior art preservation processes, it is normal to use approximately one part by volume of glycerin in a mixture with approximately two parts by volume of water, the solution being as a rule heated somewhat to obtain optimum mixture. In order that the best possible preservation in prior art processes be obtained, the preservation must be carried out during the summer while the sap is still rising in the plants. In these prior art processes, treatment times usually amount to about two weeks, an unrealistically long period of time even if the very restricted and incomplete preservation of the plants could in itself be accepted.

Furthermore, attempts have been made to increase the life of plants by spraying them with a preparation which deposits an air-permeable membrane on the plant. However, such attempts have fallen foul of the three following shortcomings: it is virtually impossible to cover every needle completely on, for example, a Juniper plant; the areas of the plant beneath the air-permeable membrane will sooner or later dry out and the resultant appearance will be completely different from that of the living plant; and as a rule a degradation process sets in in the cell matter of the plants.

The only hitherto known process of realizing complete preservation is the classical drying of plants, but this drying operation may be applied only to certain flowers and, moreover, the character of the plant is altered.

In the above-mentioned preservation process in which glycerin and water are used, dyestuffs have sometimes been added to the solution in order to replace the natural color of the plants after preservation (please see for example FR-PS No. 1,174,603 and DE-PS No. 411,406). However, it has proved to be difficult to cause the preservation mixture, and thereby the dyestuffs, to penetrate out into the shoot tips, and substantially completely fill out all of the plant cells in leaves and needles. This factor is particularly manifest as regards coniferous plants, such as the Juniperus, Pinus, Chameacyparis, Cupressus and Thuja genuses, as well as evergreen plants, such as *Hedera helix* (ivy), *Prunus laurocerasus* (cherry laurel) and *Ilex aquifolium* (holly).

It has now surprisingly proved that, in the prior art preservation process based on glycerin, water and dyestuffs, it is possible to realize, on the one hand, an industrially acceptable production process, and, on the other hand, such good preservation of plants that they, from the practical point of view, may be considered as indefinitely non-perishable, the natural properties of the plants being appreciably unchanged, if, in the dyestuff mixture, there is admixed a special, yellow dyestuff called tartrazine (E102, C.I. 19140) at a high content and, preferably, also a water-soluble potassium salt, and if this preparation is, moreover, carried out at suitable climatic conditions. It is possible, by the present invention, to realize such a total treatment of the plants right out to the outermost leaf or needle tips that the plants will retain their natural appearance and natural properties for a very long period of time.

Thus, the present invention relates to a method for preserving living plants, in particular coniferous plants apart from the Picea, Abies, Tsuga, Larix, Taxus and Cedrus genuses, in which method the plants, after cutting-off of the root, are caused to suck up, through a barked stem portion, a preservative liquid which is based on glycerin and water in the approximate volume proportions of 18:82 to 35:65 and contains colorants or dyestuffs for replacing the color of the plants after the preservation, and preferably also a water-soluble potassium salt, the plants being dried after the preservation. In the method according to the present invention, the preservation is carried out at an air temperature of from 15°–33° C. in circulating air at a relative humidity of at most 60%, the preservative liquid being kept at a temperature of from 15°–33° C.

The characterizing feature of the present invention is that the preservative liquid is caused to contain apart from a blue and possibly also a red dyestuff, tartrazine (C.I. 19140, E102) in a concentration of at least 2 g/l preservative liquid.

The method according to the present invention has been utilized for a long series of plants, of the genuses Thuja, Pinus, Juniperus, Quercus, Fagus, Ilex, Chamaecyparis, Cupressus, Prunus, Hedera, Elaeagnus and Mahonia. As examples of particular plants which have been tested and yielded very good results, mention may be made of the following:

Northern white cedar—*Thuja occidentalis* var. Columnea
Arborvitae—*Thuja occidentalis* var. Holmstrupii
Western red cedar—*Thuja plicata*
Pine—*Pinus silvestris*
Chinese juniper—*Juniperus chinensis* var. Hetzii
Common juniper—*Juniperus communis*
Savin—*Juniperus sabina*
English oak—*Quercus robur* var. Fastigiata
Beech—*Fagus silvatica*
Copper beech—*Fagus silvatica* var artopurpurea
Weeping beech—*Fagus silvatica* var. pendula
Holly—*Ilex aquifolium*
Lawson cypress—*Chamaecyparis lawsoniana* var. Alumii
True cypress—*Cupressus arizonica*
Cherryl laurel—*Prunus laurocerasus*
Ivy—*Hedera helix*
Silverberry—*Elaeagnus ebbingie*
Oregon grape—*Mahonia aquifolium*

As in the prior preservation processes, glycerin will, in the method according to the present invention, replace the water in the cell sap as regards filler and turgor. The difference between the prior art processes and that according to the present invention resides in the fact that the special yellow dyestuff, tartrazine, at the disclosed high content and the possible potassium salt, together with other preparation conditions, have resulted in a considerably more complete filling-out of the plant. As a result, the plant will be just as soft and flexible as a living plant, even though the preserved plant is in actual fact dead. It is assumed that the tartrazine, in some manner which has not been examined influences the capacity of the plants to suck up the preservative solution so that this is rapidly and effectively drawn up right out to the tips of the shoots which otherwise would remain untreated and would be destroyed. In the use of the potassium salt, in particular potassium nitrate, this high absorption capacity is further increased in a number of plants. Potassium nitrate is the preferred water-soluble potassium compound and is suitably used in a concentration of 1–15 g/l, but potassium chloride and potassium sulfate may also be used, albeit with not such good results.

If too small an amount of tartrazine is used in the colorant mixture, the result will be an incomplete preservation of the plant, whereas too high a content of tartrazine gives an incorrect and far too yellow color. In the former case the result will be a poorly preserved plant which displays poor durability and an unsightly appearance (that is to say the plant will display many brownish plant cells without preservative solution). In the latter case, a correctly preserved plant is obtained, but the appearance of the plant will be unacceptable from the commercial point of view in which the natural color is a prime factor.

The amount of blue dyestuff should be adapted to the amount of tartrazine in the preservative solution, such that a green color which is suitable for the plant in question will be obtained. In the use of patent blue V (C.I. 42051, E131) the content should be most preferably from 0.1 to 0.8 g/l. Too low or too high a content will result in commercially unacceptable yellowish or bluish preserved plants. In a corresponding manner, the posible content of red dyestuff, preferably new coccine (C.I. 16255, E124), should be adapted to the contents of the yellow and blue dyestuffs such that there will be obtained the sought-for reddish green color in the preserved plants. New coccine has the advantage that it aids the tartrazine in its effect of imparting to the plant a powerful tendency to suck up the preservative solution, such that the solution will penetrate, to an extremely high level, right out into the shoot tips of the plant. New coccine may suitably be used in a content of from 1 to 20 g/l of the preservative solution.

The proportions of water to glycerin in the preservative solution are of great importance and too high a glycerin content will render the solution far too viscous and heavy for the plant to be able to draw up the solution right out into the shoot tips. Too high a water content will, granted, entail a complete absorption of the preservative solution in the plant, but the turgor pressure will be far too low, that is to say the needles/leaves and branches of the plants will be considerably thinner than in the living state and will, moreover, be extremely brittle.

The temperature in the preservation process is also of great importance, and an air temperature of below +15° C. entails that the aspiration of the plant will be too low and that the sucking-up of the preservative liquid will be incomplete even if the treatment time were to be extended to, for example, 20 days. Too high a temperature, above 33° C., results in far too rapid a metabolism and the plant will die after about 2.5 days, with the result that the plant is incompletely preserved. The same is valid for the temperature of the preservative liquid which may vary between the above-mentioned limits. However, the preferred air temperature is +25° C., whereas the liquid temperature is suitably +28° C., since the cell aspiration of the plant will hereby commence rapidly in the preservation cycle. In order to maintain the aspiration of the plant and, consequently, the absorption of the preservative liquid, the preservation should be carried out in circulating air, the air flow velocity being preferably from 0.5 to 1 m/s past the plants partially immersed in the preservative solution. By constantly drying the flowing air, or by adding heated cold air drawn in from outside, it is possible to maintain the relative humidity of the air at the requisite low level of at most 60%. As a result of the low relative humidity, evaporation from the plant increases with a resultant increase in the taking up by suction of the preservative liquid.

In order to obtain a rapid commencement of the sucking-up of the preservation liquid and in order to ensure that the preservative liquid is, with reliability sucked right up to the shoot tips, it is advantageous if the plants, prior to immersion in the preservative liquid, are stored in the premises where the preservation method is to be carried out for up to one day before being placed in the preservative solution. In this treatment, the plants will, thus, be conditioned to substantially the same light, temperature, air flow and air humidity conditions as in the subsequent preservation method. As a result, a certain temporary wilting of the plant will be realized, such that the saline content in the plant increases, whereby an increase in the osmotic pressure will be obtained such that the sucking-up of the preservative solution takes place at extra high speed at the beginning of the preservation cycle.

In the preservation of plants during the winter when the plants are cold and a number of plants are quiescent, it is necessary, prior to the preservation, to warm and/or "wake" them. This may be effected by prewarming the plants in 100% relative humidity at approximately +30° C. for about 1 day before the plants are suspended in the premises in which the preservation takes place.

In the method according to the invention, it is preferred to conduct the preservation with the exclusion of solar light and light from a blue sky, preferably in complete darkness or in light from a cloudy sky.

The preservation period, that is to say the time from the immersion of the plants in the preservative liquid up to their complete preservation, is as a rule about five days but somewhat longer depending upon the type of plant being preserved. However, it is easy to ascertain the requisite preservation time exactly for different plant types involved. After the preservation, the plants are lifted up out of the preservative liquid and are then allowed to dry under the same climatic conditions as during the preservation cycle itself. This drying may require about five days or slightly longer. The drying operation is required in order that the natural form of the plant be retained, for, if the plants were to be packed while still damp and before they have dried, they may dry during their transport to consumers and then assume a deformed shape which the plants have while they are packed. Hence, it is essential that the major fraction of the water in the sucked-up preservative liquid be dried off.

Naturally, it is important, if a satisfactory treatment result is to be attained, that a new incision be made in the plant and that the plant, in immediate conjunction therewith, be immersed in the preservative solution so that this may freely be absorbed within all parts of the sap-transporting stem.

For the preservation of Hedera, Prunus, Elaeagnus, Ilex and Mahonia genuses and other leaf plants, and the Cupressus and Thuja genuses, the following preservative solution (No. 1) is particularly suitable.

| Water | 6400 ml |
|---|---|
| glycerin (1.23 g/cm$^3$) | 1600 ml |
| green domestic colorant$^x$ | 800 ml |
| tartrazine | 40 g |
| 3% silver nitrate aqueous solution | 16 ml |
| KNO$_3$ | 40 g |

$^x$Made by Saturnus and consisting of 1.22 weight % tartrazine (C.I. 19140, E102), 0.61 weight % patent blue V (C.I. 42051, E131), the remainder being water.

Solution No. 1 contains, thus, in total approximately 5.6 g/l of tartrazine, approximately 0.55 g/l of patent blue V and approximately 4.5 g/l KNO$_3$.

For the preservation of yellow-green Juniperus genuses (for example *Juniperus sabina* and *Juniperus chinensis pfitzeriana*) and other yellow-green coniferous plants, the following preservative solution (No. 2) is particularly suitable:

| Water | 6400 ml |
|---|---|
| glycerin (1.23 g/cm$^3$) | 1600 ml |
| green domestic colorant$^x$ | 300 ml |
| tartrazine | 16 g |
| 3% silver nitrate aqueous solution | 16 ml |
| KNO$_3$ | — |

$^x$Made by Saturnus

Thus, solution 2 contains in total approximately 2.36 g/l of tartrazine and approximately 0.22 g/l of patent blue V.

For the preservation of Thuja, Chamaecyparis, and Juniperus genuses, the following preservative solution (No. 3) is particularly suitable:

| Water | 6400 ml |
|---|---|
| glycerin (1.23 g/cm$^3$) | 1600 ml |
| green domestic colorant$^x$ | 300 ml |
| tartrazine | 16 q |
| 3% silver nitrate aqueous solution | 16 ml |
| KNO$_3$ | 40 g |

$^x$Made by Saturnus

Thus, solution No. 3 contains approximately 2.35 g/l of tartrazine, approximately 0.21 g/l or patent blue V and approximately 4.8 g/l of KNO$_3$.

Instead of the green domestic colorant purchased from Saturnus, it is possible to use other green domestic colorants which are based on tartrazine and patent blue V, for example of Ekström manufacture, as is apparent from the following Example 1.

For realizing a reddish-green color or purple color in a treated plant, it is possible also to admix with the preservative liquid a certain amount of the red dyestuff, new coccine (E124), which is apparent from the following Example 3.

The present invention will be described in greater detail below in association with a few particular Examples.

EXAMPLE 1

In this Example, a solution was prepared which consisted of 20 parts by volume of pure glycerin and 80 parts by volume of distilled water. To this solution was added 50 ml/l (0.55 g/l) of green food colorant of the Ekström manufacture. This food colorant consisted of 6 g/l food dyestuff E131 patent blue V and 10.9 g/l of food dyestuff E102 tartrazine, the remainder being water. To this solution of glycerin and water was added in addition, 3.6 g/l of extra tartrazine. Thus, the solution contained approximately 4.15 g/l of tartrazine and 0.3 g/l of patent blue V. The solution was also caused to contain 15 g/l of potassium nitrate and 1 ml/l of 3% AgNO$_3$ aqueous solution as a fungicide which was to prevent fungus attack on the preservative solution. After the preparation, the solution was kept in an open vessel in air for at least five days of oxygenation.

A Lawson cypress (*Chamaecyparis lawsoniana* var. Alumii) was sawn off at its root and suspended in the treatment premises in which the air temperature was 25° C. and the air humidity was kept as low as possible in any event below 60%. The air in the premises was changed constantly—twice per hour, and the air intake was effected over hot pipes for heating the cold outdoor air. Fans in the premises produced an air draft of 0.5-1.0 m/s past the plant which was to be preserved. After one day, approximately 10 cm of the bark around the stem at the root end was removed in order that the preservative solution be kept pure. Thereafter, a new incision surface was sawn approximately 2 cm from the earlier incision surface. Before the new incision surface had had time to be 1 min old, the lower barked end of the plant was immersed into the solution which was kept in a vessel in which the temperature of the solution was held at +28° C. by means of an immersion heater. After five days in the solution, the plant was dead and completely treated with the preservative solution, the plant being an attractive grey green color right out into all of the shoot tips. After these five days, the Lawson cypress was lifted up out of the preservative solution and allowed to hang in the treatment premises for a further five days in order to dry. After the drying, the plant could be kept for a very long time in indoor premises without displaying any visible signs of destruction. The cell content in the entire plant had, thus, been replaced by dyestuff and glycerin. Since the glycerin cannot evaporate and since it replaces the water in the cell sap of the plants as regards filler and turgor, the plant remained as soft and flexible as it had been when alive. The tartrazin and patent blue V resulted together in an attractive green color which replaced the green chlorophyll which had lost its green color on being mixed with glycerin in the plant cells. After some time the Lawson cypress was moved outdoors for the purposes of ascertaining the durability of the treatment in an outdoor climate. In these outdoor conditions, it proved that the glycerin in the cells attracted far too much moisture from the ambient air so that the entire exterior of the plant became damp. In these damp conditions, mold fungi began to grow, and after approximately four months, the plant had suffered complete degradation. Thus, the preserved plant may only be placed indoors in a reasonably moisture-free environment.

EXAMPLE 2

A 1.5 m high thuja (*Thuja occidentalis* var. Columnea) was sawn off at ground level and transported into the treatment premises. The bark was peeled off at the lower decimeter of the stem, that is to say that region of the stem which was to be immersed in the preservative solution. Within approximately 1 min. after a new saw cut having been made, the barked section of the plant was lowered into a clean vessel which contains a solution of 200 ml pure glycerin and 800 ml distilled water, this solution having been mixed with 2.2 g/l of tartrazine, 1 ml/l of 3% $AgNO_3$ aqueous solution, 15 g/l of potassium nitrate and 0.3 g/l of patent blue V. The treatment premises were held at 25° C. air temperature and the solution was maintained at a temperature of +28° C. by means of an immersion heater in order that the cell aspiration of the plant should rapidly increase. As in Example 1, an air flow past the plant of 1 m/s was maintained, the air in the premises being changed twice an hour in order to maintain the relative humidity of the air at a low level and, in any event below 60%. After 5 days is in the treatment premises, the plant was dead and completely treated, displaying an attractive green color right out into all of the shoot tips. After the treatment, the plant was lifted out of the solution and kept in the same climatic conditions for a further five days in order to dry so that it could retain its natural appearance. In this instance, the entire cell content of the plant had been replaced by color and glycerin, the proportions being such that the plant possessed its natural green color.

COMPARATIVE EXAMPLE 1

Example 2 was repeated but the air temperature was lowered to 13° C. After 14 days with the root end immersed in the preservative liquid, the plant was dead and no longer drew up any preservative solution. However, the plant was but half-treated, counting from the stem and outwardly towards the outermost shoot tips of the branches. The outer regions of all shoots were dried out and, thus, the aspiration of the plant had been far too low.

COMPARATIVE EXAMPLE 2

Example 2 was repeated but the air temperature was maintained at 35° C. As early as after 4 days, the plant had died and no longer drew up any solution. The plant was but half-treated, counting from the stem, and the outer regions of all shoots had dried out. In this case, the aspiration of the plant had been far too vigorous before the plant had been able to suck up the solution right out into the shoot tips.

COMPARATIVE EXAMPLE 3

Example 2 was repeated with the exception that the tartrazine content in the preservative solution was lowered to 0.22 g/l. After 12 days, the plant was dead and no longer drew up any solution. All parts of the plant apart from the cuticula ( =the outermost layer of the outer skin) and the epidermis (=the outer skin) were treated and the plant was, therefore, brown and not green as it should have been.

COMPARATIVE EXAMPLE 4

Example 2 was repeated, but in this case, the tartrazine content in the preservative solution was 12 g/l. After five days, the plant had died and no longer drew up any solution. The plant was fully treated right out into the shoot tips, but the plant was yellow instead of green. The plant displayed a high level of durability but was not usable from the commercial point of view if the natural green color is to be approximated.

COMPARATIVE EXAMPLE 5

Example 2 was repeated, but in this case the tartrazine content in the preservative solution was 12 g/l and patent blue V had been completely excluded. After five days, the plant had died and no longer drew up any solution. The plant was fully treated right out into the shoot tips, but the plant was bright yellow instead of green. The plant displayed a high level of durability but was not usable from the commercial point of view if the natural green color is to be approximated.

COMPARATIVE EXAMPLE 6

Example 2 was repeated with the exception that the preservative solution was composed of 400 ml of glycerin and 600 ml of distilled water. To this solution were then added the remaining component parts in the amounts disclosed in Example 2. After twelve days, the plant was dead and no longer drew up any solution. The plant proved to be but half-treated, counting from the stem. The outer regions of all shoots were dried-out and this probably depended upon the fact that the solution was far too viscous and heavy for the plant to be able to draw the solution right out to its shoot tips.

COMPARATIVE EXAMPLE 7

Example 2 was repeated with the exception that the solution was composed of 100 ml of glycerin and 900 ml of distilled water, the remaining components in the preservative solution being added in the same amounts as in Example 2. After five days, the plant was dead and no longer drew up any solution. The plant was fully treated and green but possessed but half turgor, that is to say the leaves/needles and branches were but half as thick as in the live state, and they were, moreover, very brittle.

COMPARATIVE EXAMPLE 8

Example 2 was repeated with the exception that the tartrazine dyestuff had been replaced by the basic yellow zero dye Chrysoidine in an amount of 3 g/l. After twelve days, the plant was dead and no longer drew up any solution. The plant was but partially treated, and the outer regions of all shoots were dried-out.

EXAMPLE 3

Example 2 was repeated, but in this case 15 g/l of the red dyestuff new coccine (E124, C.I. 16255) was also added to the preservative solution and the potassium nitrate content was but 2 g/l. This solution was subsequently used for the preservation of copper beech (*Fagus silvatica* var. *artropurpurea*). After five days, the plant had died and no longer drew up any solution. The plant was fully treated right out into the shoot tips and had approximately the normal red-green color. The plant displayed a very high level of durability.

EXAMPLE 4

Example 2 was repeated for the treatment of holly (*Ilex aquifolium*) instead of *thuja*. Like the *thuja* in Example 2, the holly proved to be completely treated and displayed a very high level of durability.

EXAMPLE 5

Example 2 was repeated with the exception that the content of patent blue V in the preservative solution was 0.25 g/l and the potassium nitrate content was 2 g/l and that the *thuja* has been replaced by an English oak (*Quercus robur* var. *fastigiata*). After five days in the treatment premises, the plant was dead and completely treated, displaying an attractive green color right out into the shoot tips. After a drying period of a further five days, the English oak was fully treated and it displayed a very high level of durability.

EXAMPLE 6

Example 2 was repeated, although the above-disclosed solution No. 1 was utilized in the preservation. The following plants were treated and could be preserved with excellent results:

| | |
|---|---|
| Arborvitae | *Thuja orientalis* aurea |
| true cypress | *Cypressus arizonica* |
| holly | *Ilex aquifolium* Want Toll |
| silverberry | *Elaeagnus ebbingie* |
| ivy | *Hedera helix hibernica* |
| oregon grape | *Mahonia aquifolium* |
| cherry laurel | *Prunus laurocerasus* var. |
| | rotondifolia |
| | Reynvania |
| | Caucasica |
| | Biletter |
| | Schipkaensis |
| | Makrophylla |
| | van Nes |
| | Otto Leuken |
| | Miseheana. |

Moreover, preservation was carried out, under the same conditions and with the same solution, of a crossbreed of aralia and ivy (Fatshedera), this plant having, moreover, been grafted with ivy (Hedera) at the top. This complicated plant was also preserved in a manner which was fully satisfactory for commercial purposes.

EXAMPLE 7

Example 2 was repeated, although the above-disclosed solution No. 2 was utilized in the preservation. The following plants were treated and could be preserved with excellent results.

| | | | |
|---|---|---|---|
| Chinese juniper | *Juniperus chinensis* var. | *Pfitzeriana* | |
| Chinese juniper | *Juniperus chinensis* var. | *Pfitzeriana* | aurea |
| Chinese juniper | *Juniperus chinensis* var. | *Pfitzeriana* | hetzii |
| Chinese juniper | *Juniperus chenensis* var. | *Pfitzeriana* | Old Gold |
| Savin | *Juniperus sabina* | | |

EXAMPLE 8

Example 2 was repeated, although the above-disclosed solution No. 3 was utilized in the preservation. The following plants were treated and could be preserved with excellent results.

| | |
|---|---|
| *Thuja occidentalis* var. | Emeraude |
| *Thuja occidentalis* var. | Smaragd |
| *Thuja occidentalis* var. | Holmstrupii |
| *Thuja occidentalis* var. | Little Champion |
| *Thuja occidentalis* var. | *pyramidalis compacta* |
| *Thuja occidentalis* var. | Woodwardii |
| *Thuja plicata atrovirens* | |
| *Thuja plicata zebrina* | |
| *Juniperus communis* | |
| *Juniperus communis* Suecica | |
| *Juniperus squamata* Blue Star | |
| *Juniperus squamata* Meyeri | |
| Chamaecyparies Lawsoniana var. | Lanei |
| | Stewartii |
| | Ellwoodii |
| | Delmore |
| | *Erecta viridis* |
| | Golden King |
| | Golden Wonder |
| | Stardust |
| | Tilgate |
| | Maas |
| | Pottenei |
| | Tharandtensis Caesia |
| | Alumii Gold |
| | Golden Trihent |
| | *Columnaris glauca* |
| | Silver Queen |
| | White Spot |
| | Glauca Speek |
| | Lumi |
| | Fletcherii |
| | Backhausiana |
| Chamaecyparis Lawsoniana var | Pemberi Blue |
| | Green Hedgar |
| | Wisselii |
| | Blue Surprice |
| | Ellwoods Gold |
| | Elegans |
| | Andeleynis |
| | Smithii |
| | Drummondii |
| | Witzeliana |
| | *Alumii magnifica* |
| | Westermanii |
| | Trioms van Boskoop |
| | Silver Gem |

What I claim and desire to secure by Letters Patent is:

1. In a method for preserving a living plant with a mixture of glycerin and water, the improvement wherein:
   (a) the mixture has a volume ratio of glycerin to water of approximately from 18:82 to 35:65;
   (b) the mixture has a tartrazine concentration of at least 2 grams per liter;
   (c) the mixture is maintained at a temperature of from 15° to 33° C.;
   (d) the living plant is maintained at a temperature of from 15° to 33° C. in air having a relative humidity of at most 60 percent during the method.

2. A method according to claim 1 wherein the mixture also comprises a blue dyestuff.

3. A method according to claim 1 wherein the living plant is a coniferous plant of a genus other than Picea, Abies, Tsuga, Larix, Taxus and Cedrus.

4. A method according to claim 3 wherein the plant has a severed root and which comprises immersing a portion of said plant (immediately surrounding that from which the root was severed) in the mixture and permitting said mixture to be sucked up into said plant.

5. A method according to claim 4 wherein the mixture comprises a blue dyestuff.

6. A method according to claim 5 wherein the blue dyestuff is a triphenyl methane dyestuff.

7. A method according to claim 5 wherein the blue dyestuff is patent blue V (C.I. 42501, E131).

8. A method according to claim 5 which comprises subsequent drying of the plant.

9. A method according to claim 8 wherein the mixture comprises at least one water-soluble potassium salt.

10. A method according to claim 9 wherein the blue dyestuff comprises patent blue V (C.I. 42051, E131), the mixture comprises from 2 to 10 grams per liter of patent blue V and the mixture comprises from 2 to 10 grams per liter of tartrazine.

11. A method according to claim 9 wherein the mixture comprises additional dyestuff to replace plant color after preservation.

12. A method according to claim 11 wherein the mixture comprises a red dyestuff.

13. A method according to claim 12 wherein the red dyestuff comprises new coccine (C.I. 16255, E124).

14. A method according to claim 13 wherein the water-soluble potassium salt is potassium nitrate, which is present in the mixture in a concentration of from 1 to 15 grams per liter.

15. A liquid plant-preservative composition comprising glycerin, water and tartrazine, the glycerin and water being in a ratio of from about 18:82 to about 35:65 by volume and the tartrazine being in a concentration of at least 2 grams per liter.

16. A liquid plant-perservative composition according to claim 15 containing dyestuff for replacing color of plant parts, including a blue dyestuff.

17. A liquid plant-preservative composition according to claim 16 wherein the blue dyestuff comprises a triphenyl methane dyestuff.

18. A liquid plant-preservative composition according to claim 16 wherein the blue dyestuff comprises patent blue V (C.I. 42051, E131).

19. A liquid plant-preservative composition according to claim 15 comprising a water-soluble potassium salt.

20. A liquid plant-preservative composition according to claim 15 comprising a blue dyestuff and a red dyestuff.

21. A liquid plant-preservative composition according to claim 20 comprising a water-soluble potassium salt.

22. A liquid plant-preservative composition according to claim 21 wherein the red dyestuff is new coccine (C.I. 16255, E124).

23. A liquid plant-preservative composition according to claim 21 which comprises from 2 to 10 grams per liter of tartrazine.

24. A liquid plant-preservative composition according to claim 23 wherein the blue dyestuff comprises patent blue V in a concentration of from 0.1 to 0.8 gram per liter.

25. A liquid plant-preservative composition according to claim 21 wherein the water-soluble potassium salt is potassium nitrate in a concentration of from 1 to 15 grams per liter.

* * * * *